United States Patent
Laghi

(10) Patent No.: US 6,579,323 B2
(45) Date of Patent: *Jun. 17, 2003

(54) RATCHET TYPE PROSTHETIC LOCK

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 0 days.

This patent is subject to a terminal disclaimer.

(21) Appl. No.: 10/064,823

(22) Filed: Aug. 21, 2002

(65) Prior Publication Data

US 2003/0023321 A1 Jan. 30, 2003

Related U.S. Application Data

(62) Division of application No. 09/618,511, filed on Jul. 18, 2000, now Pat. No. 6,511,513.

(51) Int. Cl.[7] .............................. A61F 2/60; A61F 2/78
(52) U.S. Cl. ........................................... 623/33; 623/36
(58) Field of Search ...................................... 623/32–38

(56) References Cited

U.S. PATENT DOCUMENTS

| 5,226,918 A | 7/1993 | Silagy et al. |
| 6,051,026 A | 4/2000 | Biedermann et al. |
| 6,106,559 A | 8/2000 | Meyer |
| 6,361,569 B1 | 3/2002 | Slemker et al. |

*Primary Examiner*—Corrine McDermott
*Assistant Examiner*—Will Matthews
(74) *Attorney, Agent, or Firm*—Ronald E. Smith; Smith & Hopen, P.A.

(57) ABSTRACT

A prosthetic lock assembly of the ratchet type for connecting a liner for a prosthetic socket to a prosthesis. The lock assembly includes a two part locking mechanism held together by suitable fasteners. Removal or loosening of the fasteners enables a user to separate the two parts from one another in the event a sock gets into and jams the locking mechanism. In a first set of four embodiments, a latch is formed in a first part of the locking mechanism and in a second set of four embodiments, the latch is formed in a second part of the locking mechanism. The lock assembly may be mounted internally or externally of the prosthetic socket. The first part of the locking mechanism may be a laminating ring or a thermoforming plate and the second part may be a mounting block with or without a pyramid for controlling a prosthetic pylon.

4 Claims, 8 Drawing Sheets

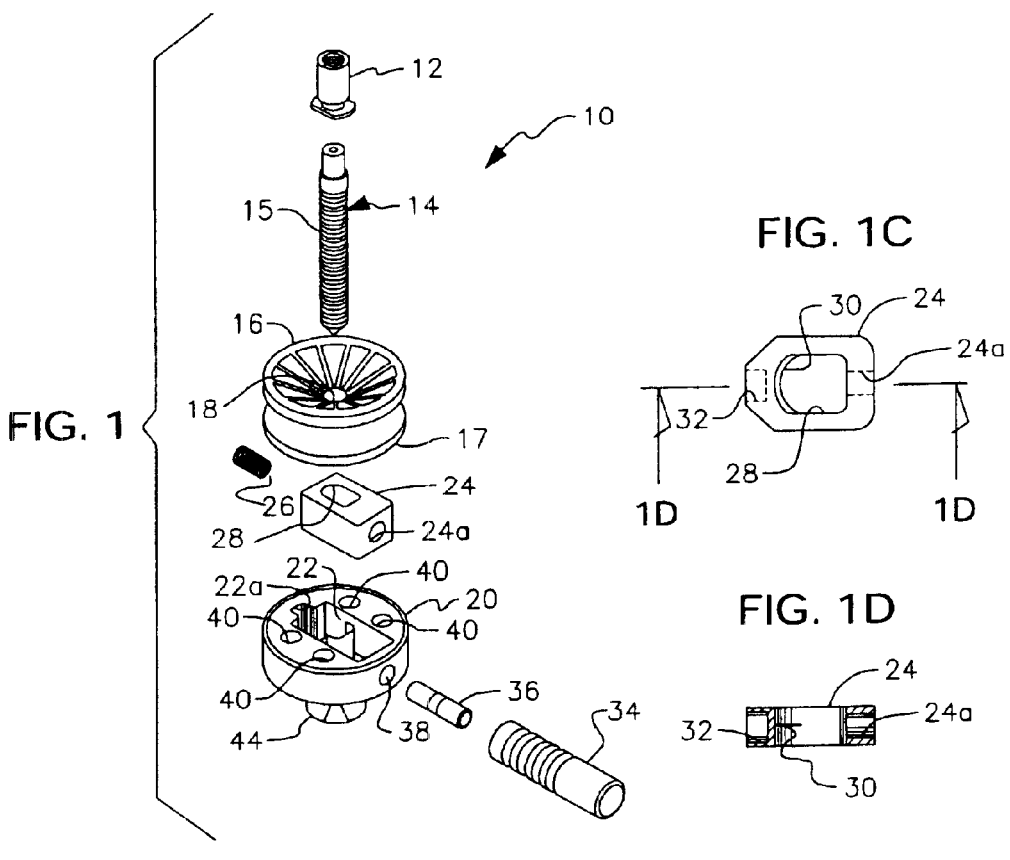
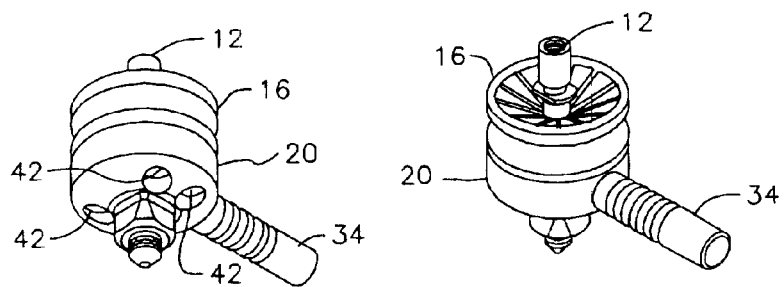

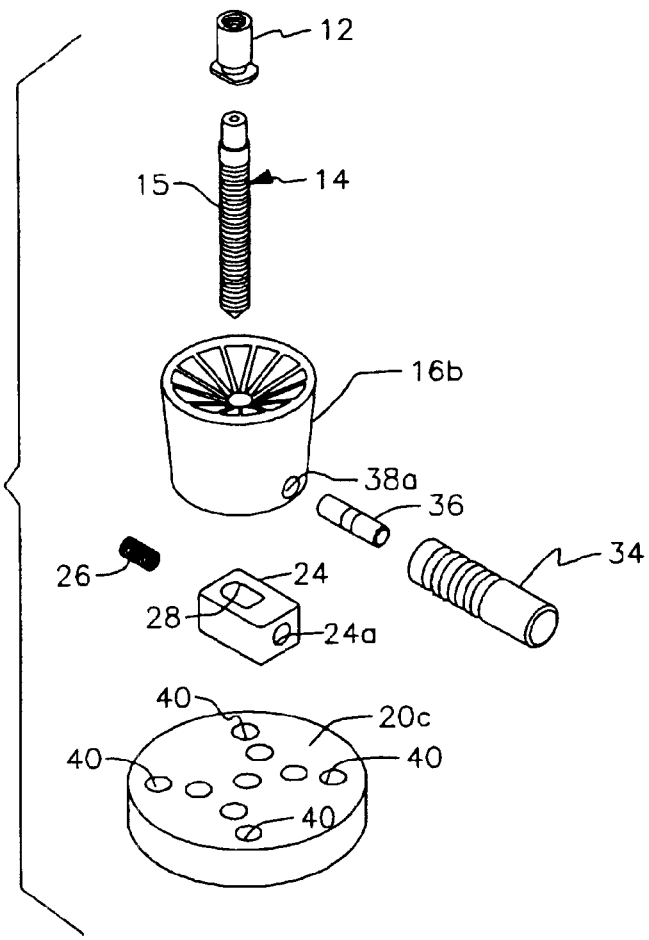
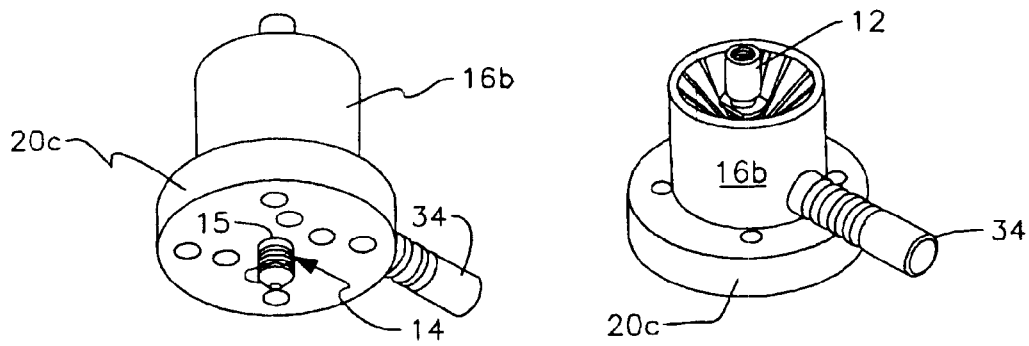
FIG. 6
FIG. 6A
FIG. 6B

RATCHET TYPE PROSTHETIC LOCK

RELATED APPLICATIONS

This disclosure is a division of a disclosure of the same title by the same inventor, filed Jul. 18, 2000, bearing Ser. No. 09/618,511 now U.S. Pat. No. 6,511,513.

BACKGROUND OF THE INVENTION

1. Field of the Invention

This invention relates, generally, to prosthetic locking devices. More particularly, it relates to a prosthetic lock of the ratchet type.

2. Description of the Prior Art

A prosthetic locking device is positioned at the distal end of a prosthetic socket. Its function is to enable releasable locking of a socket liner of the type worn on a residual limb to a prosthetic device such as an artificial leg and foot assembly. More particularly, an aperture is formed in a prosthetic socket at a distal end thereof for receiving a serrated, elongate locking pin therethrough. The elongate locking pin is engaged to the distal end of a socket liner. A locking means is positioned between the distal end of the socket and the proximal end of the prosthetic device. The locking means releasably engages the elongate locking pin, thereby interconnecting the socket liner and the prosthetic device.

There are two different types of prosthetic locking devices in current use. The first type is known as the ratchet type and the second is known as the clutch type. In a ratchet type lock, a serrated, elongate locking pin is selectively engaged by a pawl. In a clutch type, a serrated, elongate locking pin is engaged by the teeth of a movably mounted gear that can rotate only in one direction.

The primary drawback of a ratchet type lock derives from the distance between serrations; a socket slack is created whereby the residual limb moves up and down as the patient walks. Another drawback arises when a patient accidentally jams a prosthetic sock into the hole of the lock. The sock disables the ratchet and pawl locking mechanism and the socket can be removed only by cutting it off, thereby destroying it. This type of jamming is a very common occurrence.

The primary drawback of a clutch type prosthetic lock is that it has a greater height extent than a ratchet type lock, to accommodate the height of the one-way gear. Moreover, its operation is silent. Most amputees dislike this feature of clutch type locks because they prefer the reassuring clicking sound made by a ratchet type lock when it is positively engaged.

What is needed, then, is a ratchet type lock that provides a reassuring audible feedback when it is positively seated, but which has a low profile. Moreover, the new ratchet lock should enable removal of a residual limb from a socket, even if a prosthetic sock has become lodged in the locking means.

However, in view of the prior art in at the time the present invention was made, it was not obvious to those of ordinary skill in the pertinent art how the identified needs could be fulfilled.

SUMMARY OF INVENTION

The longstanding but heretofore unfulfilled need for an improved ratchet type locking assembly is now met by a new, useful, and nonobvious invention. The novel locking assembly interconnects a prosthetic socket liner to a pylon that forms a part of a prosthetic leg. An elongate locking pin depends from a distal end of the socket liner and extends into releasable locking engagement with the novel lock assembly through an opening formed in the distal end of the prosthetic socket.

In all embodiments, the novel lock assembly includes two major parts that abut one another and which are held in such abutting relationship by suitable fasteners. Removal or at least loosening of the fasteners enables total or at least partial separation of said two major parts, respectively. When fully or partially separated, any jamming problems that may occur may be overcome in the absence of any need to cut the prosthetic socket.

The first major part may take the form of a laminating ring or a thermoforming plate. The former is used where the prosthetic socket is a carbon or fiberglass laminate and the latter is used where the prosthetic socket is a thermoformed plastic.

The second major part may take the form of a lock body with an integral pyramid for controlling the pylon or a lock body without a pyramid. Embodiments with integral pyramids save space and cost by combining the lock, mounting plate, and the pyramid or prior art deigns into a single piece. The embodiments with pyramids are subjected to side loads at heel strike.

The second major part may also take the form of a mounting plate with a pyramid or without a pyramid. The novel latch means that engages the elongate locking pin may be positioned within the first major part or the second major part of the lock assembly. Moreover, the lock assembly may be mounted within a prosthetic socket or externally thereof.

In a first embodiment, the novel prosthetic lock assembly for interconnecting a liner for a prosthetic socket with a pylon that forms a part of a leg prosthesis includes a first major part in the form of a laminating ring having a central bore formed therein. The central bore has a longitudinal axis substantially coincident to a longitudinal axis of the prosthetic socket liner. An elongate latching pin depends from the liner and is adapted to be slidingly received within the central bore. The elongate latching pin has a plurality of closely spaced apart, annular ratchet means formed therein along the length thereof. The annular ratchet means are disposed normal to a longitudinal axis of the elongate latching pin. As mentioned above, an opening is formed in the distal end of the prosthetic socket and the elongate latching pin extends through that opening to engage the novel lock assembly.

In the first embodiment, for use with laminated prosthetic sockets, the novel lock assembly includes a lock body having an integral pyramid. The lock body abuttingly engages a laminating ring and fastener means are provided for releasably interconnecting the laminating ring and the lock body. A latching means is formed in the lock body for releasably engaging an elongate latching pin. In this way, the socket liner is connected to the prosthetic device when the elongate latching pin is engaged by the latching means. Loosening or removal of the fastener means enables separation of the laminating ring and the lock body so that jamming of the latching means by a sock may be overcome in the absence of a need to cut off the socket.

A latching block that forms a part of the novel latching means is positioned in an opening formed in the lock body. The latching block is adapted to engage the elongate latching pin between contiguous ratchets of the annular ratchet means and to hold the elongate latching pin against longitudinal movement when so engaged. The opening has an extent in a preselected dimension greater than an extent of the latching block in a corresponding dimension so that the latching block has a first position at a first end of the opening, a second position at a second end of the opening, and an infinite plurality of positions therebetween.

A bias means is positioned within the opening and urges the latching block into engaging relation to the elongate latching pin when the bias means is in repose. A release means for overcoming the bias means is provided so that the elongate latching pin is removable from the lock body and hence from the laminating ring when the release means is activated.

The release means further includes a bore formed in an annular peripheral edge of the lock body. The bore is disposed radially with respect to the longitudinal axis of the prosthetic liner. A push button means extends through the bore and a first end of the push button means abuttingly engages the latching block and a second end of the push button means projects radially outwardly from the bore so that a user can press the second end of the push button means and displace the latching block, overcoming the bias of the bias means, thereby disengaging the latching block from the elongate latching pin so that the liner may be removed from the prosthetic socket.

In a second embodiment, the lock ring has no pyramid. In a third embodiment, used in conjunction with a plastic socket, a thermoforming plate replaces the laminating ring but the locking plate still has a pyramid. In a fourth embodiment, the thermoforming plate replaces the laminating ring and the locking plate has no pyramid.

All of the first four embodiments are mounted externally relative to the prosthetic socket. Four additional embodiments are disclosed, each of which is positioned within the prosthetic socket. In the final four embodiments, the latching block is positioned in an opening formed in the laminating ring or the thermoforming plate. Accordingly, the laminating ring in such embodiments is referred to as the laminating lock body and the thermoforming plate is referred to as the thermoforming lock body. The part corresponding to the lock body of the first four embodiments is referred to as a mounting plate with pyramid or a mounting plate without pyramid because it performs no locking function in said embodiments. However, it is releasably engaged to the laminating lock body or the thermoforming lock body with fasteners as in the first four embodiments. Thus, the anti-jamming feature is provided in all eight embodiments.

A primary object of this invention is to provide a ratchet type prosthetic locking device that does not require cutting of a socket when the locking device is jammed.

Another important object is to provide a ratchet type locking device so that users thereof are assured by audible clicking sounds that the device is working.

Another object is to provide such a device of the type that can be mounted inside or outside of a prosthetic socket and which may be provided with or without an integral pyramid for controlling a pylon.

Another important object is to provide a ratchet type locking device having a reduced longitudinal extent relative to ratchet type locking devices of the prior art.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is an exploded view of a first embodiment of the invention;

FIG. 1A is a first perspective view of said first embodiment in its assembled configuration;

FIG. 1B is a second perspective view of said first embodiment in its assembled configuration;

FIG. 1C is a top plan view of the latching block;

FIG. 1D is a sectional view taken along line 1D—1D on FIG. 1C;

FIG. 6 is an exploded view of a sixth embodiment of the invention;

FIG. 6A is a first perspective view of said sixth embodiment in its assembled configuration;

FIG. 6B is a second perspective view of said sixth embodiment in its assembled configuration;

DETAILED DESCRIPTION

Figure 2:
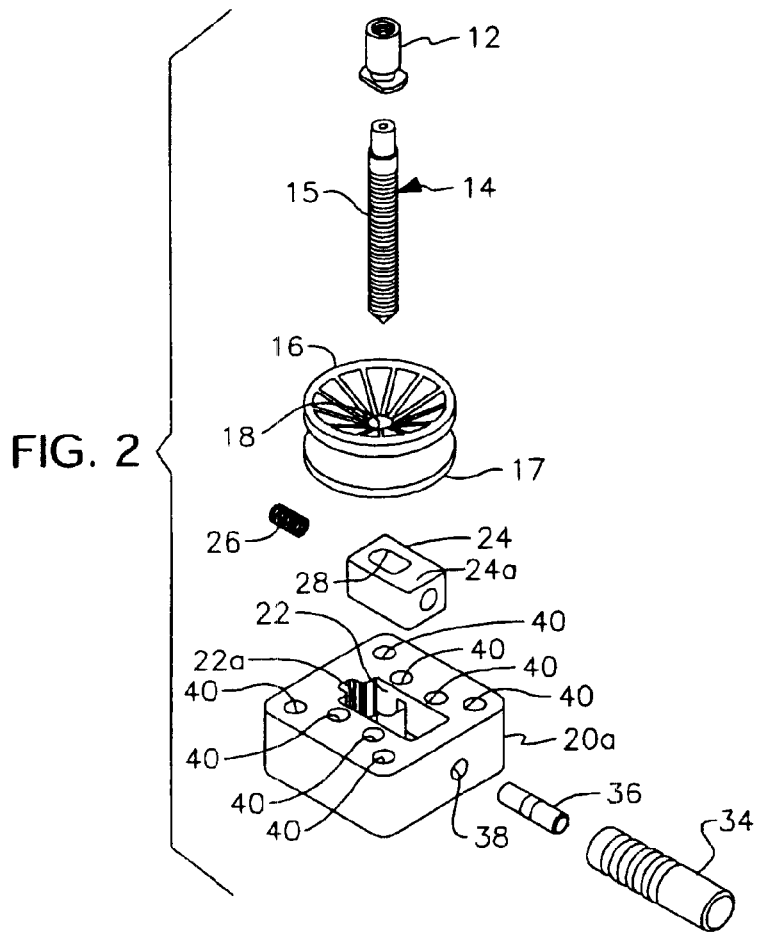
FIG. 2 is an exploded view of a second embodiment of the invention.

Referring now to FIG. 1, it will there be seen that the reference number 10 denotes a first illustrative embodiment of the present invention.

In this first embodiment, the latching mechanism is external to the socket and is preferably formed of stainless steel. Reducer 12 surmounts and screw threadedly engages latching pin 14. Latching pin 14 is attached by suitable means, not shown, to the distal end of a socket liner, not shown, and extends through an aperture formed in the distal end of a prosthetic socket, not shown. A plurality of closely, equidistantly spaced, annular serrations 15 are formed in latching pin 14.

Laminating ring 16 is centrally apertured as at 18 to receive latching pin 14 therethrough. Laminating ring 16 is placed onto the distal end of a positive cast of the patient's residual limb and secured into position with the components of a fabrication kit, not shown. A laminating fabric is draped onto the cast and tied around the laminating ring. A laminating resin is then applied and allowed to cure.

Lock body 20 is formed independently of laminating ring 16 and is disposed in abutting, underlying relation thereto when novel prosthetic locking means 10 is assembled, as perhaps best understood in connection with FIGS. 1A and 1B. An opening 22 is formed in lock body 20 and extends therethrough. The size and shape of opening 22 is sufficient to accommodate therein a latching block 24 and a latching spring 26. An opening 28 extends through latching, block 24 and a sharp ridge 30 extends from a peripheral edge of said opening as best understood in connection with FIGS. 1C and 1D. Blind bore 32 is formed in a rear wall of latching block 24 to accommodate a first end of latching spring 26. Opening 22 of lock body 20 includes a narrow extended part 22a that accommodates the second end of said latching spring when the novel locking mechanism is assembled. Therefore, when latching spring 26 is in repose, it urges latching block 24 and hence sharp ridge 30 into abutting engagement with latching pin 14 such that said sharp ridge 30 is disposed between two of said serrations 15. Sharp ridge 30 fully occupies the space between the serrations and there is therefore no slack to cause pistoning when the patient walks.

When it is desired to disengage sharp ridge 30 from locking pin 14, push button handle 34 is manually depressed. A first end of push button rod 36 is in screw threaded engagement with an internally threaded bore formed in said push button handle 34. A second end of push button rod 36 is in screw threaded engagement with an internally threaded bore 24a formed in latching block 24. Push button rod 36 extends through unthreaded bore 38 formed in the peripheral edge of lock body 20. In this way, depression of push button handle 34 displaces latching block 24, compressing latching spring 26, so that sharp edge 30 disengages from serrations 15 and enables withdrawal of locking pin. 14 from aperture 18 formed in laminating ring 16.

When push button handle 34 is released, locking spring 26 unloads and returns latching block 24 to its position of repose within lock body 20. This positions sharp edge 30 in the path of travel of serrations 15 when latching pin 14 is reintroduced through aperture 18. Such reintroduction causes latching spring 26 to quickly load and unload, i.e., to become compressed and expanded, as said serrations pass by. The sharp edge 30 thus enters into each space between the serrations and withdraws therefrom as they travel by. Each entrance, under the bias provided by latching spring 26, produces the characteristic clicking sound of a ratchet type prosthetic lock. This sound reassures the wearer that the locking mechanism is working. When the last click is heard, the wearer knows that latching pin 14 is fully inserted into lock body 20.

This novel latching means reduces the profile of the novel locking means, relative to prior art locking means, because it occupies the same plane as the lock body.

Although a good socket liner provides a sufficient cushion between a residual limb and a prosthetic socket, some patients prefer to position a sock over the liner for further comfort. An opening is formed in the distal end of the sock to accommodate latching pin 14. Accordingly, the sock can enter into opening 18 formed in laminating ring 16 and jam the locking mechanism. The formation of laminating ring 16 and lock body 20 as two separate parts solves this problem. A plurality of openings, collectively denoted 40 in FIG. 1, are formed in lock body 20. Each opening 40 has a longitudinal axis parallel to the longitudinal axis of latching pin 14. A matching plurality of internally threaded openings are formed in bottom wall 17 of laminating ring 16, and screws 42 (FIG. 1A) interconnect said lock body 20 and said laminating ring 16. In the event of a jam, whether caused by a sock or other foreign matter, said screws 42 are loosened or removed, allowing lock body 20 to disconnect from laminating ring 16. This allows the bias provided by the sock to overcome the bias of latching spring 26 and the sock can be removed from opening 18 in the absence of any need to cut the prosthetic socket.

Pyramid 44 depends from lock body 20 and provides orientation for a pylon of a prosthetic leg, not shown.

Lock body 20 replaces the conventional lock, mounting plate, and conventional pyramid of the prior art and enables the provision of a ratchet type locking means having a much lower profile, or longitudinal extent, than the ratchet type locking means of the prior art, by combining said parts into a single low profile part.

Figure 2A:
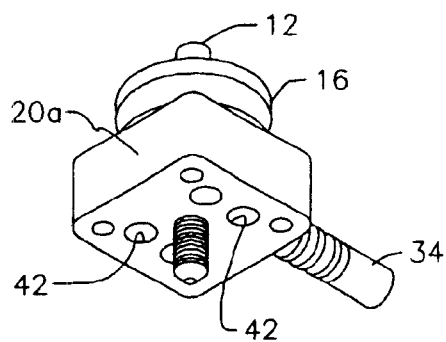
FIG. 2A is a first perspective view of said second embodiment in its assembled configuration.
Figure 2B:
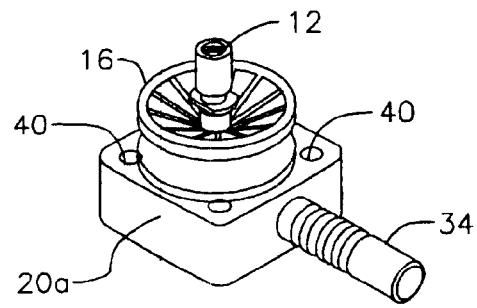
FIG. 2B is a second perspective view.of said second embodiment in its assembled configuration.

The second embodiment of the invention is depicted in FIGS. 2, 2A, and 2B. It differs from the first embodiment in that it has a flat lock body 20a with no integral pyramid, but all other parts are the same as indicated by the same reference numerals. Accordingly, a conventional pyramid is attached to said lock body 20a. Lock body 20a represents an improvement over the prior art because it combines the conventional lock and the conventional mounting plate into a single part having a smaller profile or longitudinal extent than the combined profiles of the prior art lock and mounting plate.

Figure 3:
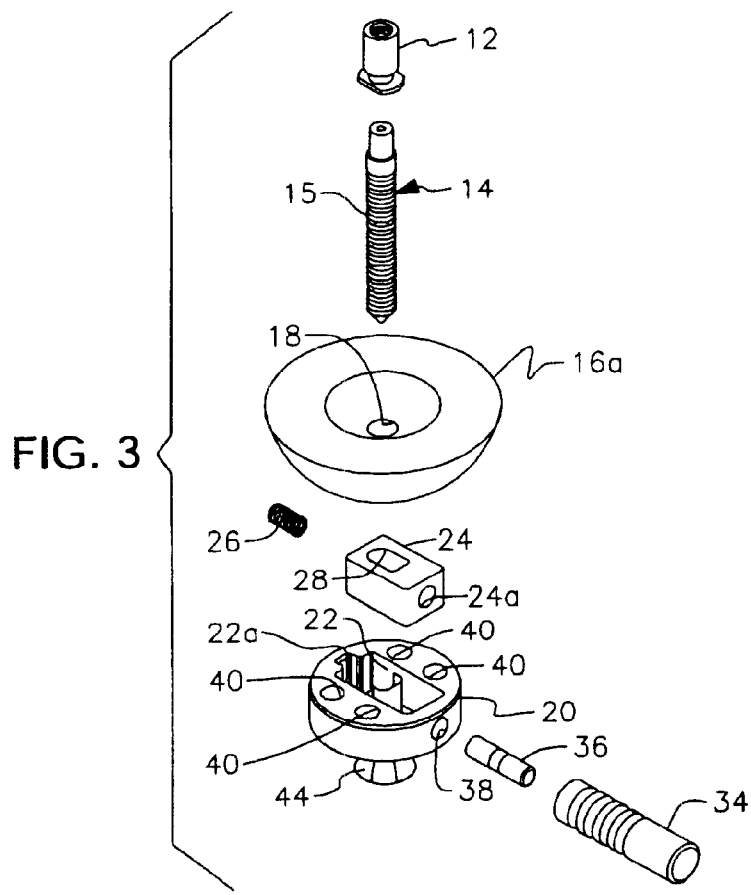
FIG. 3 is an exploded view of a third embodiment of the invention.
Figure 3A:
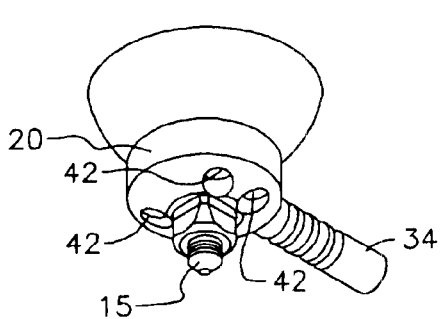
FIG. 3A is a first perspective view of said third embodiment in its assembled configuration.
Figure 3B:
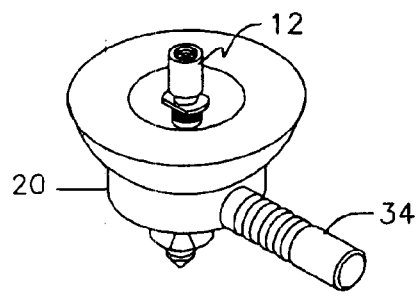
FIG. 3B is a second perspective view of said third embodiment in its assembled configuration.

The third embodiment of the invention is depicted in FIGS. 3, 3A, and 3B. The assembly is externally mounted, is preferably formed of titanium, and includes a pyramid for pylon control. All of the parts are the same as in the first embodiment, with the exception that laminating ring 16 is replaced by thermoforming plate 16a that is placed onto the distal end of the positive cast of the residual limb and secured in place with the components of the fabrication kit. The thermoplastic for the socket is heated in an oven and then drape formed or vacuum formed onto the cast and the support plate.

Figure 4:
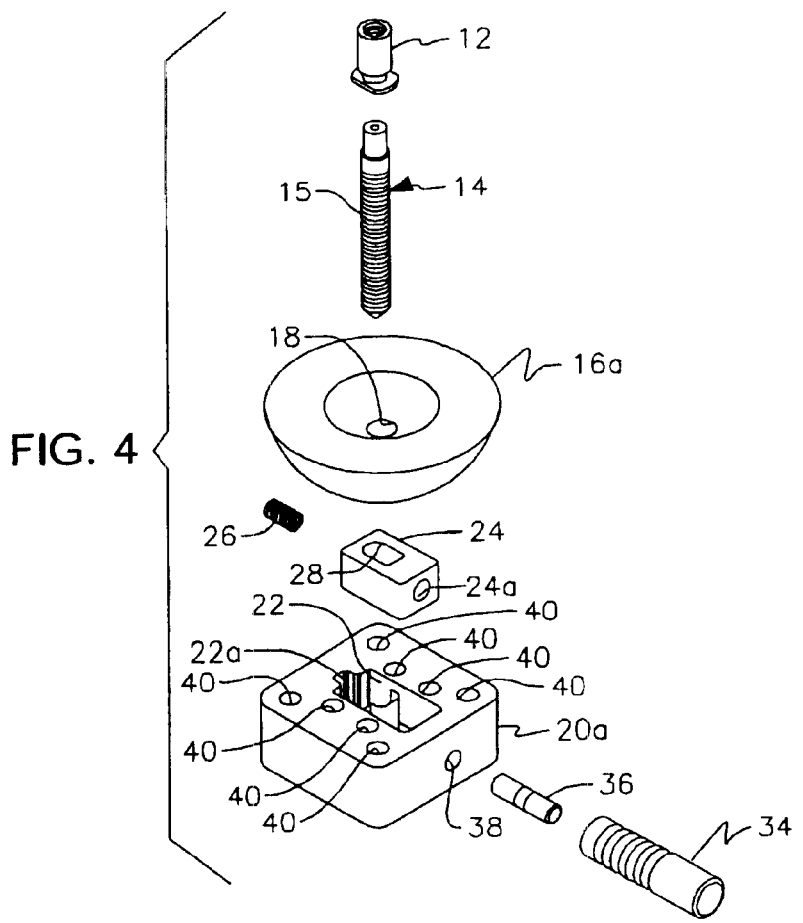
FIG. 4 is an exploded view of a fourth embodiment of the invention.
Figure 4A:
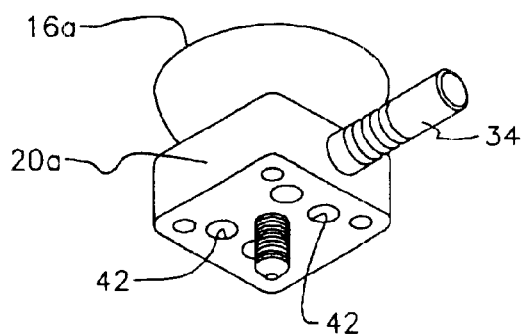
FIG. 4A is a first perspective view of said fourth embodiment in its assembled configuration.
Figure 4B:
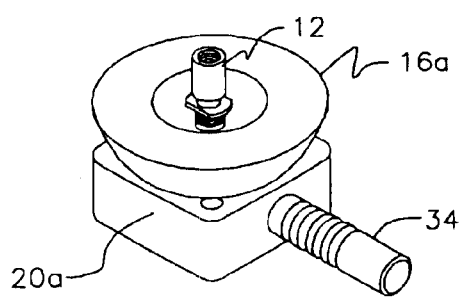
FIG. 4B is a second perspective view of said fourth embodiment in its assembled configuration.

FIGS. 4, 4A, and 4B depict the fourth embodiment. It includes thermoforming plate 16a of the third embodiment and the flat lock body 20a of the second embodiment. The assembly is externally mounted, is preferably formed of titanium, and has no integral pyramid.

Figure 5:
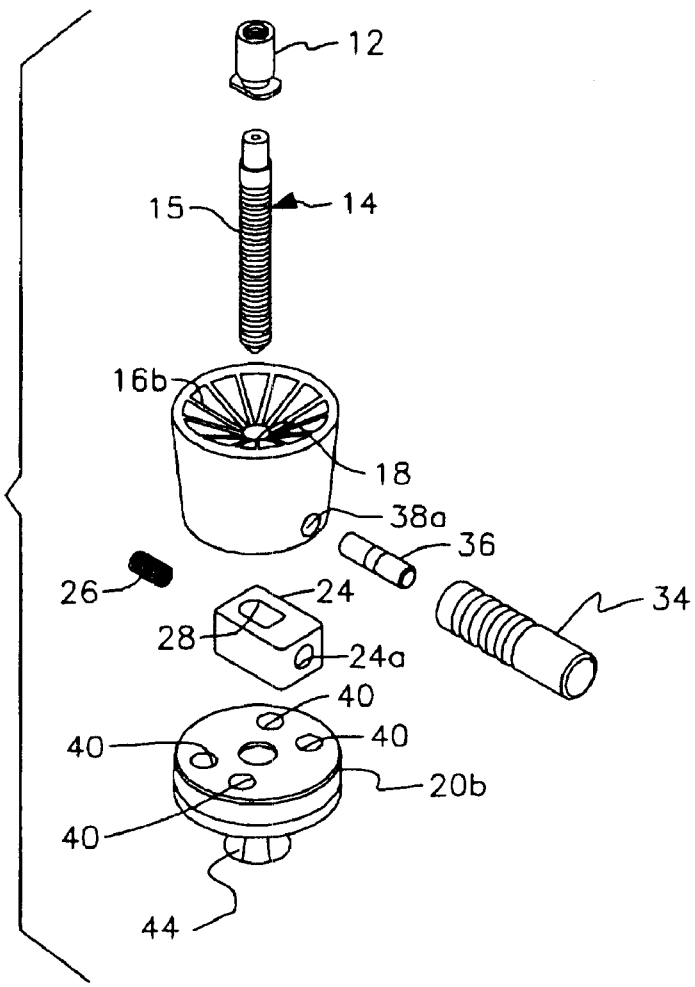
FIG. 5 is an exploded view of a fifth embodiment of the invention.
Figure 5A:
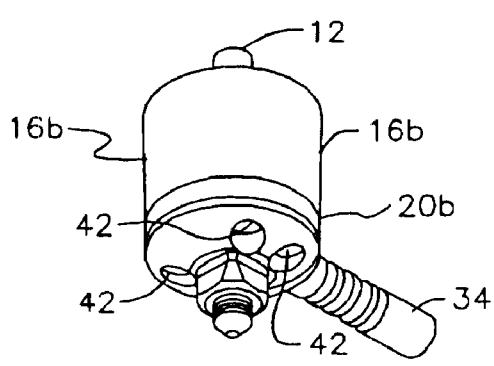
FIG. 5A is a first perspective view of said fifth embodiment in its assembled configuration.
Figure 5B:
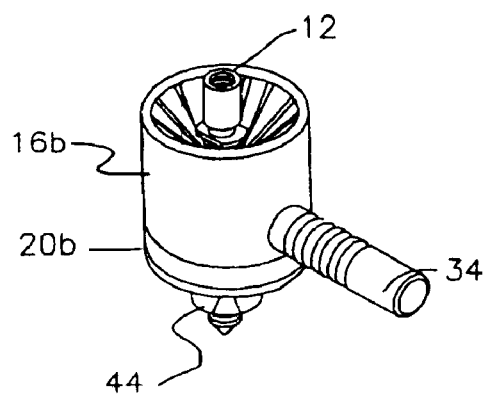
FIG. 5B is a second perspective view of said fifth embodiment in its assembled configuration.

The lock-assembly of the fifth embodiment, depicted in FIGS. 5, 5A, and 5B, is internally mounted and preferably formed of stainless steel. Latching block 24 and latching spring 26, in this embodiment, are positioned in a cavity formed in laminating lock body 16b, which has tapered sidewalls, and not in lock body 20 or 20a as in the externally-mounted embodiments just described. Accordingly, an internally threaded opening 38a is formed in a peripheral edge of said laminating lock body 16b and not in said lock body 20 or 20a. Due to the internal mounting, it is necessary to provide a means for preventing laminating resin from fouling the latching mechanism. The means includes a pushbutton dummy, not shown, that is screwed into a laminating lock dummy, not shown. Fasteners are employed to fasten the laminating lock dummy to mounting plate 20b and said laminating lock body 16b is laminated into the socket. A cut out is then formed in the socket to expose the pushbutton dummy which is then unscrewed and removed from the laminating lock dummy.

The fasteners are then removed so that the laminating lock dummy and mounting plate are disconnected. The laminating lock dummy is then replaced with real laminating lock body 16b and the real pushbutton rod 36 is screwed into said real laminating lock body 16b.

Note that mounting plate 20b is circumscribed by a laminating ring.

This fifth embodiment shares the same advantages as that of the first embodiment, and includes further advantages as well. Specifically, lateral stresses resulting from heel strikes or other activities are not transferred from mounting plate 20b to the socket by means of fasteners. Instead, the stresses are transferred from mounting plate 20b to the socket directly through laminating lock body 16b. This increases the weight rating of the lock whereas the strength rating of the fasteners would reduce said weight rating. Moreover, the fasteners between mounting plate 20b and laminating lock body 16b are not subjected to lateral stress but only to the weight of the prosthesis. Such weight represents only a nominal force.

The sixth embodiment, depicted in FIGS. 6, 6A, and 6B, is also internally mounted and dummy parts are used to avoid fouling the latch mechanism. It shares the same structure and advantages as the fifth embodiment in all respects except that it includes mounting plate 20c which has no integral pyramid.

Figure 7:
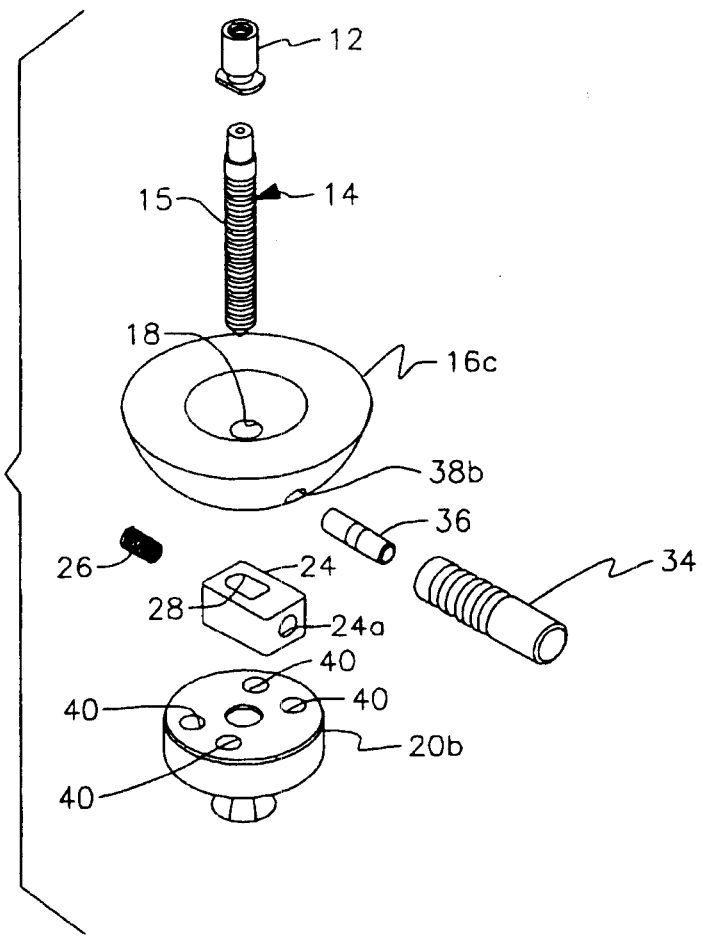
FIG. 7 is an exploded view of a seventh embodiment of the invention.
Figure 7A:
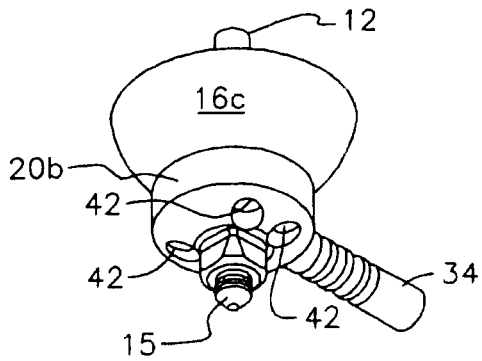
FIG. 7A is a first perspective view of said seventh embodiment in its assembled configuration.
Figure 7B:
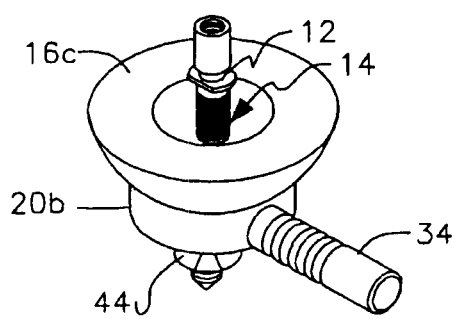
FIG. 7B is a second perspective view of said seventh embodiment in its assembled configuration.

FIGS. 7, 7A, and 7B depict the seventh embodiment. It is similar to the third and fourth embodiments in that it includes thermoforming lock body 16c and is different from said third and fourth embodiments in that the latching means is positioned within said thermoforming lock body 16c. It includes mounting plate 20b having pyramid 44.

Figure 8:
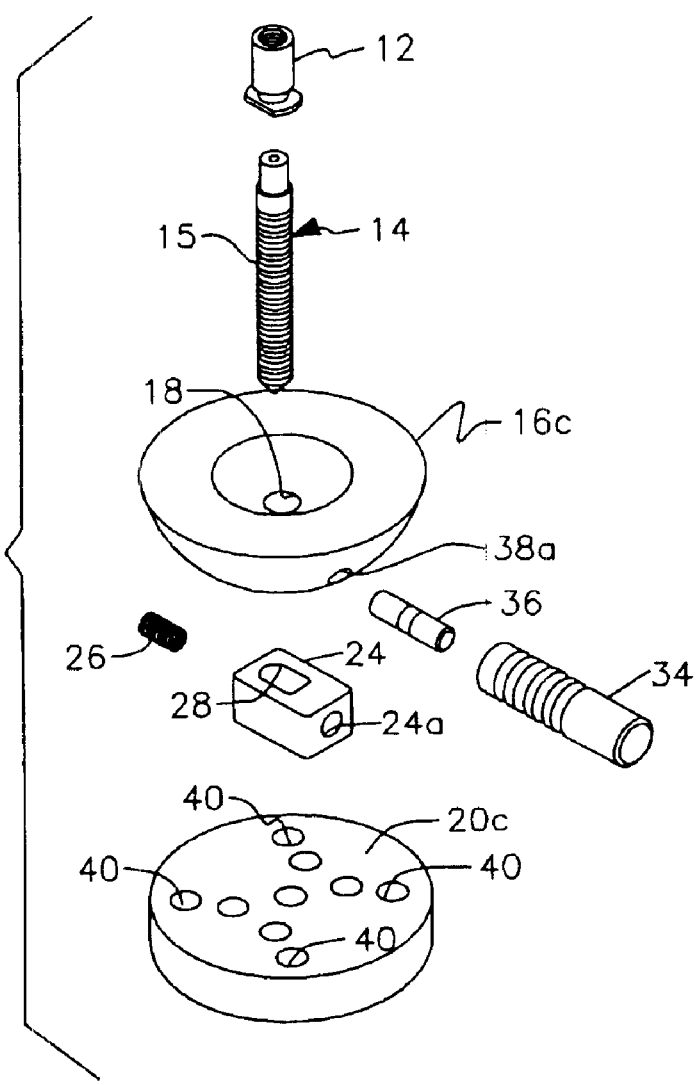
FIG. 8 is an exploded view of an eighth embodiment of the invention.
Figure 8A:
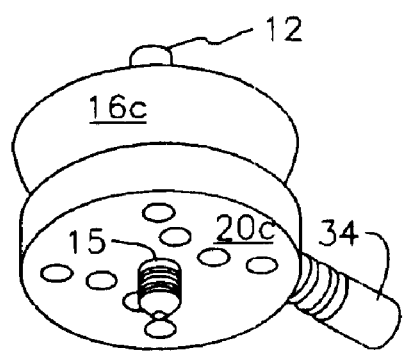
FIG. 8A is a first perspective view of said eighth embodiment in its assembled configuration.
Figure 8B:
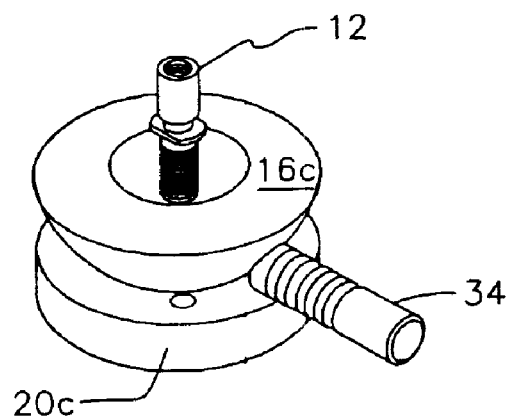
FIG. 8B is a second perspective view of said eighth embodiment in its assembled configuration.

The final embodiment is depicted in FIGS. 8, 8A, and 8B. It includes thermoforming lock body 16c of the seventh embodiment and mounting plate 20c with no pyramid of the sixth embodiment.

All of the embodiments provide the desired clicking noise when the elongate locking pin is being inserted into the locking means, and all of the embodiments have a lower profile than the ratchet type and clutch type locking devices heretofore known. Moreover, the inventive structure is the first, anywhere in the world, to enable jams of the locking mechanism to be overcome in the absence of any need to cut a prosthetic socket. The inventive structure is also highly versatile, being usable with laminated or plastic sockets, and being mountable externally or internally of a socket.

It will be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A prosthetic lock assembly for interconnecting a liner for a prosthetic socket with a prosthesis, comprising:
   a thermoforming plate having a central bore formed therein, said central bore having a longitudinal axis substantially coincident to a longitudinal axis of said prosthetic socket liner;
   an elongate latching pin adapted to be slidingly received within said central bore, said elongate latching pin having a plurality of closely spaced apart, annular ratchet means formed therein along the length thereof, said annular ratchet means being disposed normal to a longitudinal axis of said elongate latching pin;
   said elongate latching pin adapted to depend from a distal end of said prosthetic socket liner;
   a lock body adapted to abuttingly engage said thermoforming plate;
   fastener means for releasably interconnecting said thermoforming plate and said lock body;
   latching means formed in said lock body for releasably engaging said elongate latching pin;
   an opening formed in said lock body;
   a centrally apertured latching block disposed within said opening;
   said latching block adapted to engage said elongate latching pin between contiguous ratchets of said annular ratchet means and to hold said elongate latching pin against longitudinal movement when so engaged;
   said opening having an extent in a preselected dimension greater than an extent of said latching block in a corresponding dimension so that said latching block has a first position at a first end of said opening, a second position at a second end of said opening, and an infinite plurality of positions therebetween;
   a bias means positioned within said opening, said bias means urging said latching block into engaging relation to said elongate latching pin when said bias means is in repose; and
   release means for overcoming said bias means so that said elongate latching pin and hence said socket liner are removable from said lock body and hence from said thermoforming plate when said release means is activated;
   whereby said liner is connected to said prosthesis when said elongate latching pin is engaged by said latching means; and
   whereby loosening or removal of said fastener means enables separation of said thermoforming plate and said lock body so that jamming of said latching means by a sock may be overcome in the absence of a need to cut off said socket.

2. The prosthetic lock assembly of claim 1, wherein said release means further comprises:
   a bore formed in an annular peripheral edge of said lock body, said bore being disposed radially with respect to said longitudinal axis of said prosthetic liner;
   a push button means that extends through said bore, a first end of said push button means abuttingly engaging said latching block and a second end of said push button means projecting radially outwardly from said bore;
   whereby a user presses said second end of said push button means and displaces said latching block, overcoming the bias of said bias means, thereby disengaging said latching block from said elongate latching pin so that said liner may be removed from said prosthetic socket.

3. The prosthetic lock assembly of claim 1, wherein said thermoforming plate and said lock body are positioned externally to said socket.

4. The prosthetic lock assembly of claim 1, wherein said thermoforming plate and said lock body are positioned within said socket.

* * * * *